(12) United States Patent
Shepherd et al.

(10) Patent No.: US 12,629,272 B2
(45) Date of Patent: May 19, 2026

(54) MODULAR KNEE BRACE ASSEMBLY

(71) Applicant: Ortho Innovations, LLC, Selbyville, DE (US)

(72) Inventors: Bryan Shepherd, Selbyville, DE (US); Eugene Welch, Selbyville, DE (US); Edward Spirko, Selbyville, DE (US); Morris B. Polsky, Selbyville, DE (US)

(73) Assignee: Ortho Innovations, LLC, Selbyville, DE (US)

( * ) Notice: Subject to any disclaimer, the term of this patent is extended or adjusted under 35 U.S.C. 154(b) by 403 days.

(21) Appl. No.: 17/987,361

(22) Filed: Nov. 15, 2022

(65) Prior Publication Data

US 2023/0071145 A1      Mar. 9, 2023

Related U.S. Application Data

(63) Continuation of application No. 16/533,127, filed on Aug. 6, 2019, now Pat. No. 11,771,577.

(51) Int. Cl.
*A61F 5/01* (2006.01)
*A47C 20/02* (2006.01)
*A61F 5/058* (2006.01)

(52) U.S. Cl.
CPC .......... *A61F 5/0106* (2013.01); *A47C 20/021* (2013.01); *A61F 2005/0167* (2013.01); *A61F 5/0585* (2013.01)

(58) Field of Classification Search
CPC .... A61F 5/0106; A61F 5/0585; A61F 5/0111; A61F 5/013; A61F 5/0127; A61F 5/0113; A61F 2005/0167; A61F 13/061; A61F 13/062; A61F 13/065; A61F 13/066; A47C 20/021; A43B 7/141; A43B 7/142; A43B 7/143; A43B 17/14; A43B 17/16
USPC .............. 602/16, 26, 27, 65; 128/882; 36/44
See application file for complete search history.

(56) References Cited

U.S. PATENT DOCUMENTS

| | | | |
|---|---|---|---|
| 3,604,023 A | 9/1971 | Lynch |
| 4,041,940 A | 8/1977 | Frankel |
| 4,697,583 A | 10/1987 | Mason et al. |
| 4,765,318 A | 8/1988 | Tranberg et al. |
| 4,889,109 A | 12/1989 | Gifford |

(Continued)

FOREIGN PATENT DOCUMENTS

KR            200457050 Y1 *  12/2011  ............... A43B 7/02

*Primary Examiner* — Alireza Nia
*Assistant Examiner* — Michael Milo
(74) *Attorney, Agent, or Firm* — Dickinson Wright PLLC

(57) ABSTRACT

A modular joint brace assembly comprising a brace and a wedge is disclosed. The brace comprises a first panel, a second panel, a third panel, and a first mating unit coupled to a top surface of the brace. The first mating unit comprises a first portion, a second portion, and a third portion. The wedge comprises a first top surface, a second top surface, and a peak, wherein the first top surface adjoins the second top surface to form the peak; and a second mating unit coupled to the first top surface and the second top surface, wherein the second mating unit is adapted to couple with the first portion, the second portion, and the third portion of the first mating unit such that the peak of the wedge aligns with a back portion of a user's joint thereby supporting at least one or more portions of the user's body.

20 Claims, 5 Drawing Sheets

(56)             References Cited

U.S. PATENT DOCUMENTS

| | | | | |
|---|---|---|---|---|
| 4,910,818 | A * | 3/1990 | Grabill | A47C 20/021 |
| | | | | 5/494 |
| 5,125,123 | A * | 6/1992 | Engle | A47C 20/025 |
| | | | | 128/845 |
| 5,216,771 | A * | 6/1993 | Hoff | A47C 20/025 |
| | | | | 5/652 |
| D347,476 | S * | 5/1994 | McDonald | D24/190 |
| 5,418,991 | A | 5/1995 | Shiflett | |
| 6,640,368 | B2 | 11/2003 | Roston | |
| 6,935,697 | B2 | 8/2005 | Conion | |
| D646,790 | S | 10/2011 | Castillo | |
| 9,084,704 | B2 * | 7/2015 | Oberst | A61G 7/075 |
| 9,775,440 | B1 * | 10/2017 | Chon | A47C 20/021 |
| 2007/0094800 | A1 * | 5/2007 | Hensley | A47C 20/021 |
| | | | | 5/648 |
| 2007/0185423 | A1 * | 8/2007 | Brown | A61F 5/0106 |
| | | | | 602/5 |
| 2012/0284901 | A1 * | 11/2012 | Webb | A41D 13/065 |
| | | | | 2/227 |
| 2017/0197818 | A1 | 7/2017 | Berreklouw | |
| 2017/0360586 | A1 | 12/2017 | Demper et al. | |
| 2018/0214295 | A1 * | 8/2018 | Davis | A61F 5/0113 |
| 2021/0267320 | A1 | 9/2021 | Yamashita et al. | |

* cited by examiner

MODULAR KNEE BRACE ASSEMBLY

CROSS-REFERENCE TO RELATED APPLICATIONS

This application is a continuation of U.S. patent application Ser. No. 16/533,127 filed on Aug. 6, 2019, the entire disclosure of which is incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable.

STATEMENT REGARDING PRIOR DISCLOSURES BY THE INVENTOR OR JOINT INVENTOR

Not Applicable.

BACKGROUND OF THE INVENTION

Field of the Invention

Description of Related Art including information disclosed under 37 CFR 1.97 and 1.98.

The disclosure and prior art relates to knee brace devices and more particularly pertains to a new knee brace device for supporting a knee in a plurality of sleeping positions.

BRIEF SUMMARY OF THE INVENTION

An embodiment of the disclosure meets the needs presented above by generally comprising a brace that is worn around a knee after orthopedic surgery has been performed on the knee. A wedge is removably coupled to the brace when the brace is worn around the knee. The wedge is positioned on a back side of the knee to support the knee in a bent position when the user is lying on the user's back. An inner knee support is removably coupled to the brace when the brace is worn around the knee. The inner knee support extends between each of the user's knees when the user lies on their side. An outer knee support is removably coupled to the brace when the brace is worn around the knee. In this way the outer knee support supports the knee when the user lies on theuser's side.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
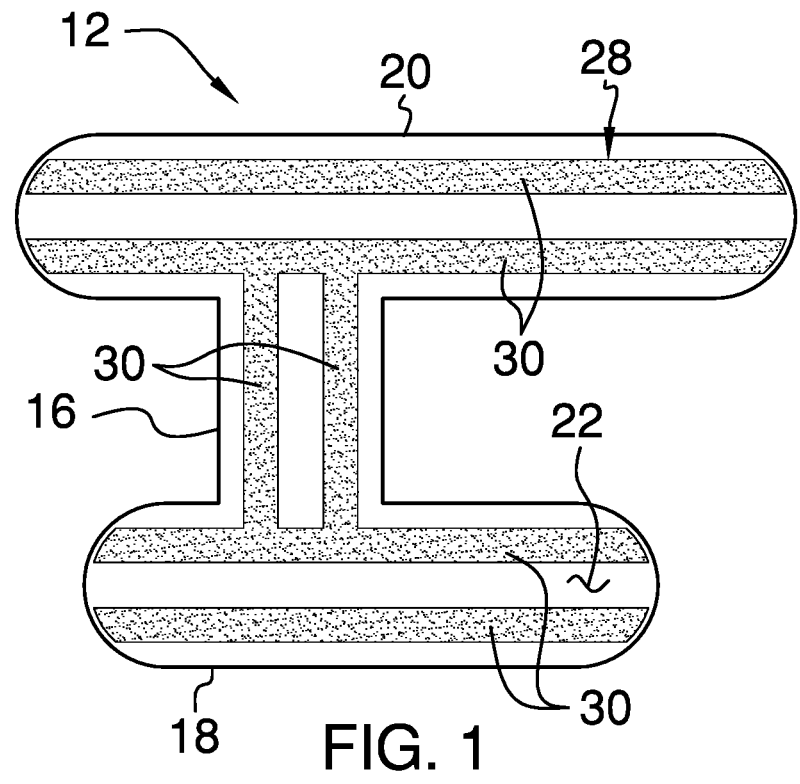
FIG. 1 is a top view of a brace of a modular knee brace assembly according to an embodiment of the disclosure.
Figure 2:
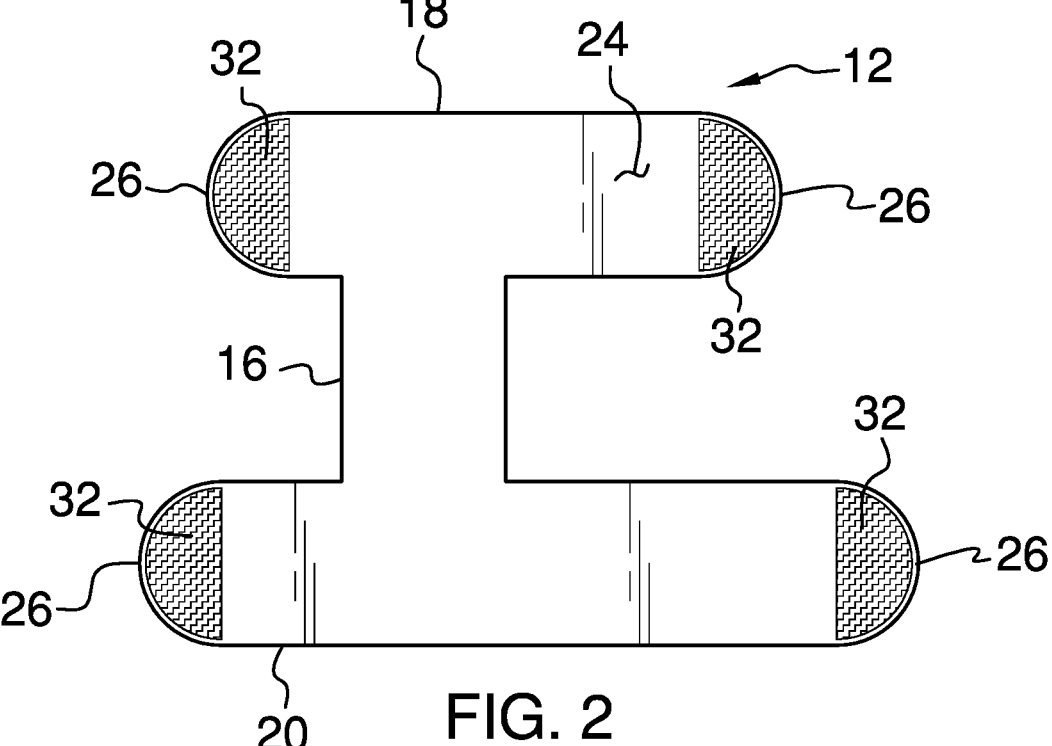
FIG. 2 is a bottom view of a brace of an embodiment of the disclosure.
Figures 3, 4, 5:
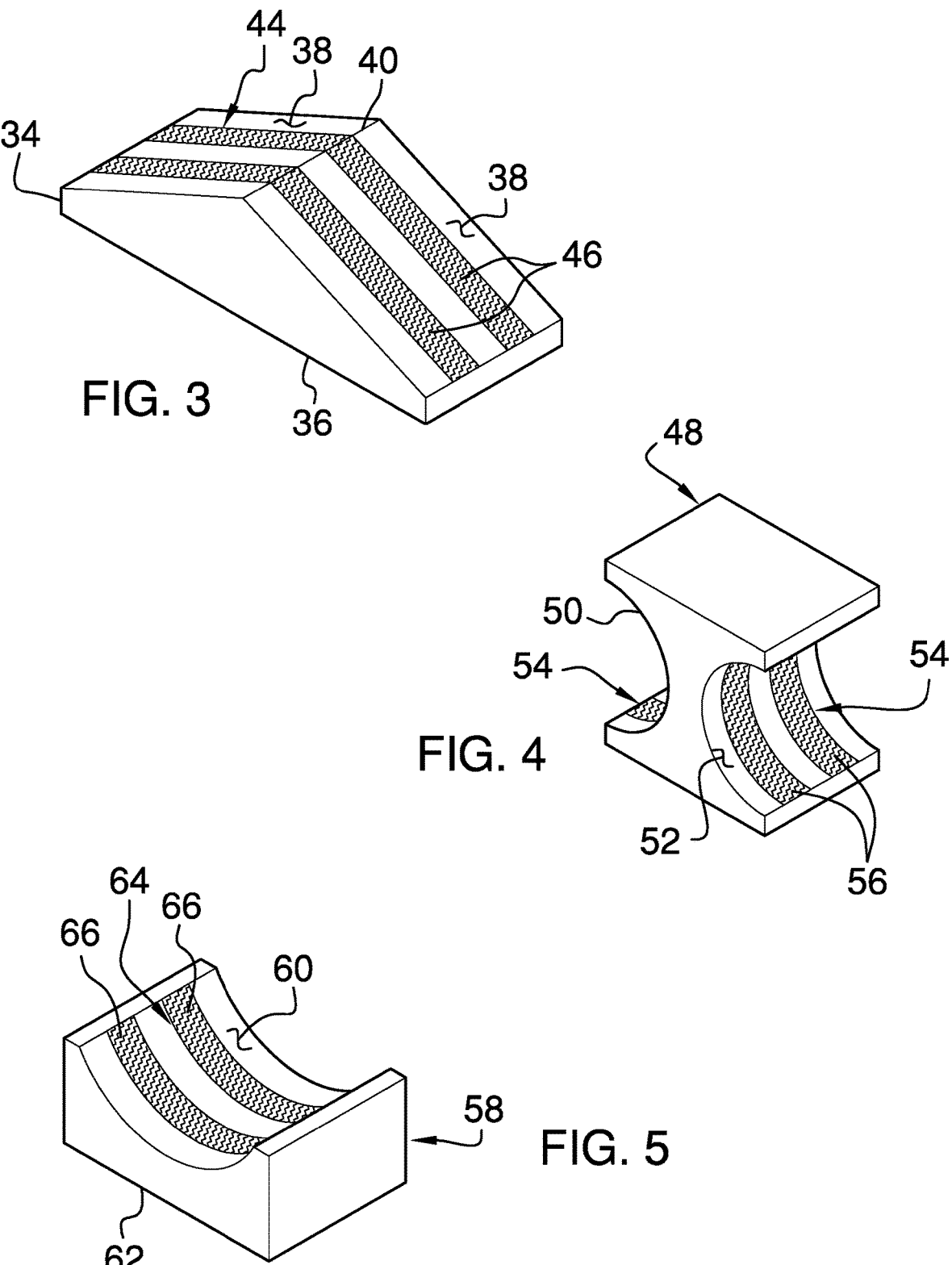
FIG. 3 is a top perspective view of a wedge of an embodiment of the disclosure.
FIG. 4 is a front perspective view of an inner knee support of an embodiment of the disclosure.
FIG. 5 is a perspective view of an outer knee support of an embodiment of the disclosure.

With reference now to the drawings, and in particular to FIGS. 1 through 8 thereof, a new knee brace device embodying the principles and concepts of an embodiment of the disclosure and generally designated by the reference numeral 10 will be described.

As best illustrated in FIGS. 1 through 8, the modular knee brace assembly 10 generally comprises a brace 12 that is worn around a knee 14 after orthopedic surgery has been performed on the knee 14. The brace 12 comprises a first panel 16 extending between a second panel 18 and a third panel 20. The first panel 16 is oriented at a right angle with each of the second 18 and third 20 panels such that the brace 12 has an I shape. Additionally, the first panel 16 extends along an axis that is offset from a lateral centerline of each of the second 18 and third 20 panels. The second panel 18 has a lengththat is shorter than a length of the third panel 20.

Each of the first 16, second 18 and third 20 panels has a top surface 22 and a bottom surface 24, and each of the second 18 and third 20 panels has a pair of distal ends 26 with respect to the first panel 16. The bottom surface 24 is wrapped around the knee 14 having the top surface 22 being exposed. The second panel 18 is wrapped around the user's upper calf, the third panel 20 is wrapped around the user's lower thigh and the first panel 16 extends vertically along a back of the user's knee 14.

A first mating unit 28 is coupled to the brace 12 and the first mating unit 28 is exposed when the brace 12 is worn around the knee 14. The first mating unit 28 comprises a plurality of sets of strips 30. Each of the sets of strips 30 is positioned on thetop surface 22 of a respective one of the first 16, second 18 and third 20 panels.

Moreover, each of the sets of strips 30 is coextensive with the respective first 16, second 18 and third 20 panels. The set of strips 30 on the first panel 16 intersects the set of strips 30 on each of the second 18 and third 20 panels.

A plurality of mating members 32 is each coupled to the brace 12. Each of the mating members 32 releasably engages the first mating unit 28 when the brace 12 is wrapped around the knee 14 for retaining the brace 12 around the knee 14. Each of the mating members 32 is positioned on the bottom surface 24 of a respective one of the second 18 and third 20 panels. Additionally, each of the mating members 32 is aligned with a respective one of the distal ends 26 of the respective second 18 and third 20 panels. Each of the mating members 32 releasably engages the set of strips 30 on the respective second 18 and third 20 panels. Each of the mating members 32 and each of the strips 30 may comprise hook and loop fasteners or the like.

A wedge 34 is removably coupled to the brace 12 when the brace 12 is worn around the knee 14. The wedge 34 is positioned on a back side of the knee 14 to support the knee 14 in a bent position when the user is lying on the user's back. The wedge 34 has a basal surface 36 extending between a pair of top surfaces 38, and the top surfaces 38 are oriented at an angle with each other. Each of the top surfaces 38 abuts the top surface 22 of a respective one of the second 18 and third 20 panels when the brace 12 is worn on the knee 14. A peak 40 of the top surfaces 38 is aligned with a back of the knee 14 thereby supporting the knee 14 in a bent position. The basal surface 36 abuts a support surface 42 upon which the user is lying thereby supporting the knee 14 in the bent position. The wedge 34 may be comprised of a resiliently compressible material for enhancing comfort for the user.

A second mating unit 44 is coupled to the wedge 34 and the second mating unit 44 releasably engages the first mating unit 28 to retain the wedge 34 on the brace 12. The second mating unit 44 comprises a set of strips 46 that is positioned on each of the top surfaces 38 of the wedge 34. The set of strips 46 of the second mating unit 44 is coextensive with each of the top surfaces 38 of the wedge 34. Moreover, each of the strips 46 of the second mating unit 44 releasably engages respective ones of the strips 30 of the first mating unit 28. Each of the strips 46 of the second mating unit 44 may comprise hook and loop fasteners or the like.

An inner knee support 48 is removably coupled to the brace 12 when the brace 12 is worn around the knee 14. The inner knee support 48 extends between each of the user's knees 14 when the user lies on their side. Moreover, the inner knee support 48 is positioned on an interior side of the knee 14 to support the knee 14 when the user lies on their side opposite of the knee 14 on which the brace 12 is worn. The inner knee support 48 has a first lateral surface 50 and a second lateral surface 52. Each of the first 50 and second 52 lateral surfaces is concavely arcuate with respect to each other to conform to the curvature of a respective one of the user's knees 14 when the user lies on the user's side. The inner knee support 48 is positioned on the user's thigh above the knee 14. The inner knee support 48 may be comprised of a resiliently compressible material for enhancing comfort for the user.

A pair of third mating units 54 is each coupled to the inner knee support 48. Respective ones of the third mating units 54 releasably engage the first mating unit 28 to retain the inner knee support 48 on the brace 12. Each of the third mating units 54 comprises a set of strips 56 and each of the strips 56 of each of the third mating units 54 is positioned on a respective one of the first 50 and second 52 lateral surfaces of the inner knee support 48. Each of the strips 56 on a respective one of the first 50 or second 52 lateral surfaces releasably engages respective ones of the strips 30 of the first mating unit 28. Additionally, each of the strips 56 of the third mating units 54 may comprise a hook and loop fastener or the like.

An outer knee support 58 is removably coupled to the brace 12 when the brace 12 is worn around the knee 14 to support the knee 14 when the user lies on the user's side. The outer knee support 58 is positioned on an outer side of the knee 14 to support the knee 14 when the user lies on the outer side of the knee 14. The outer knee support 58 has a first surface 60 that is concavely arcuate with respect to a second surface 62 such that the first surface 60 can conform to the curvature of the knee 14. The second surface 62 abuts the support surface 42 when the user lies on the user's side. The outer knee support 58 may be comprised of a resiliently compressible material to enhance comfort for the user.

A fourth mating unit 64 is coupled to the outer knee support 58. The fourth mating unit 64 releasably engages the first mating unit 28 to retain the outer knee support 58 on the brace 12. The fourth mating unit 64 comprising a set of strips 66 and each of the strips 66 of the fourth mating unit 64 is positioned on the first surface 60 of the outer knee support 58. Each of the strips 66 of the fourth mating unit 64 releasably engages respective ones of the strips 30 of the first mating unit 28. Additionally, each of the strips 66 of the fourth mating unit 64 may comprise a hook and loop fastener or the like.

Figure 6:
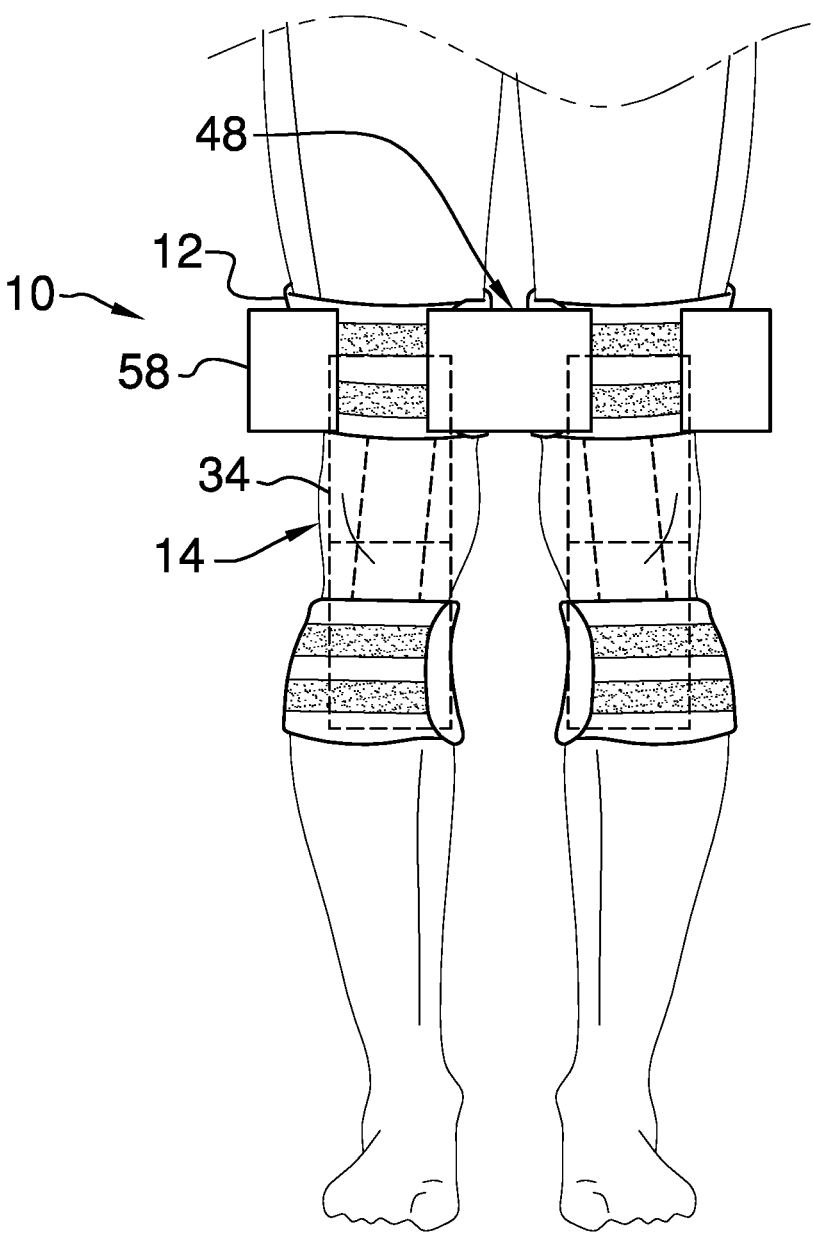
FIG. 6 is a front in-use view of an embodiment of the disclosure.
Figure 7:
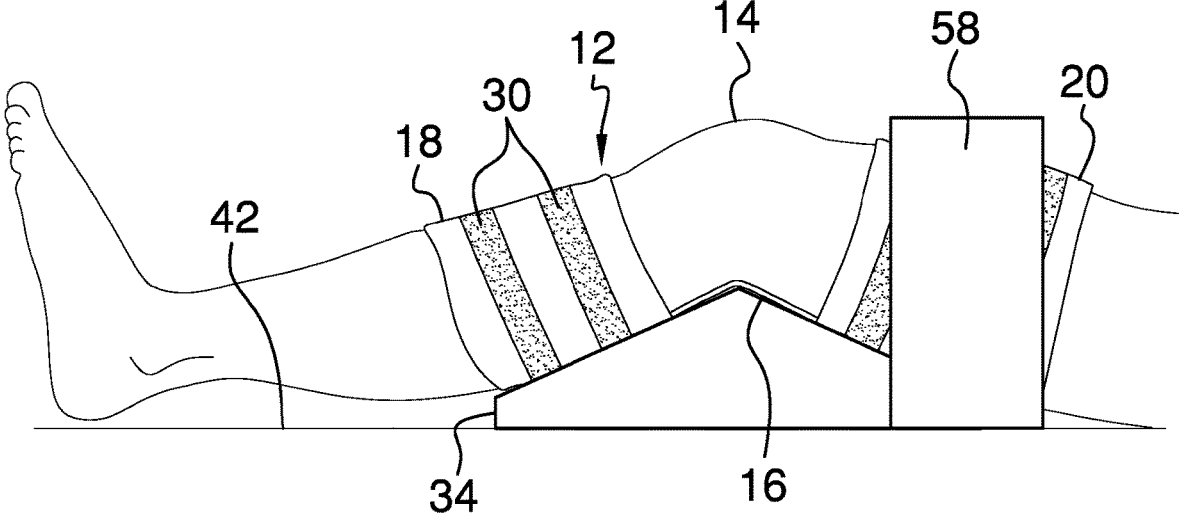
FIG. 7 is a perspective in-use view of an embodiment of the disclosure.
Figure 8:
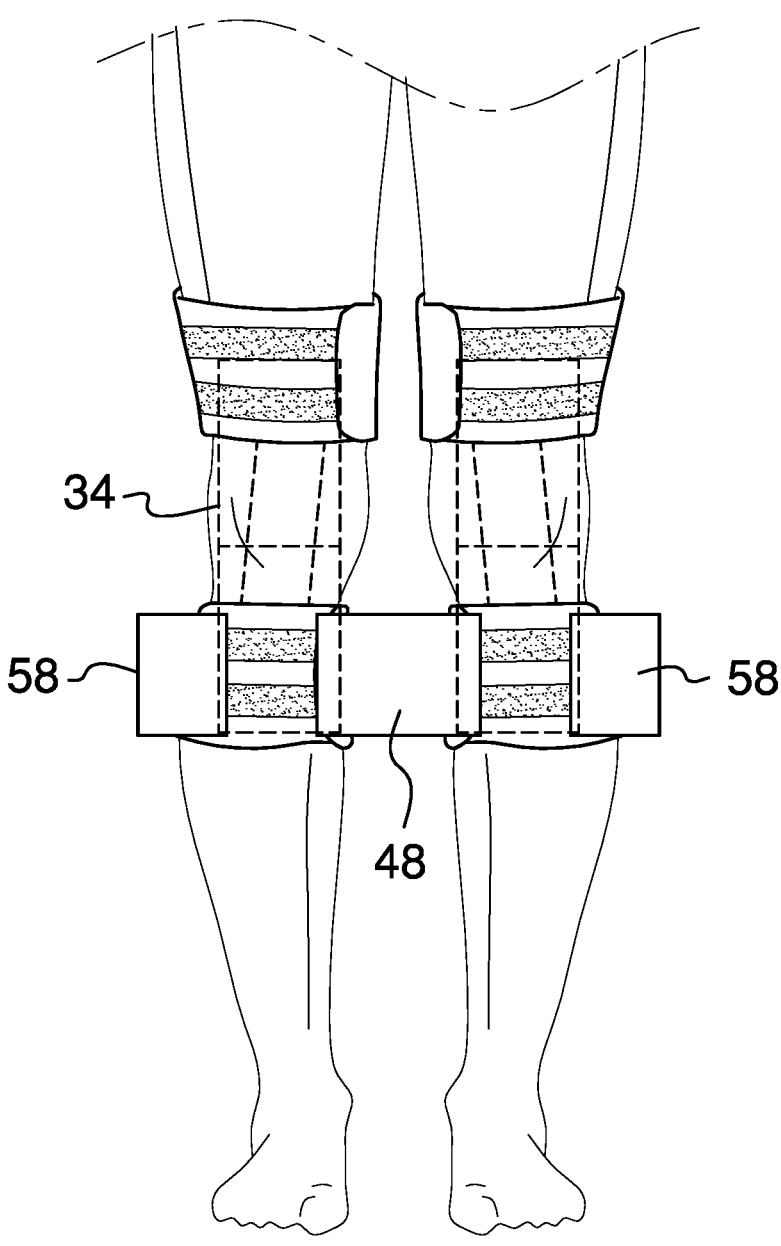
FIG. 8 is a front perspective in-use view of an embodiment of the disclosure.

As is most clearly shown in FIG. 6, a pair of the braces 12 may each be worn around a respective one of the user's knees 14. The inner knee support 48 can be coupled between each of the braces 12. Additionally, a pair of the outer knee supports 58 may each be coupled to a respective one of the braces 12. In this way each of the knees 14 are supported regardless of which side the user is lying on. A pair of the wedges 34 may eachbe coupled to a respective one of the braces 12 to support each of the knees 14 when the user is lying on their back. As is most clearly shown in FIG. 8, the inner knee support 48 and the outer knee support 58 can be aligned with each of the user's knees.

In use, the brace 12 is worn around the user's knee 14. The wedge 34 is coupled to the brace 12 and the wedge 34 is positioned on the back side of the knee 14. The inner knee support 48 is coupled to the brace 12 and the inner knee support 48 is positioned on the interior side of the knee 14. The outer knee support 58 is coupled to the brace 12 and the outer knee support 58 is positioned on the outer side of the knee 14 support. In this way the user's knee 14 is supported regardless if the user is sleeping on their back, their right side or their left side. Moreover, the brace 12, the wedge 34, the inner knee support 48 and the outer knee support 58 reduce pain during sleeping and enhance the healing process.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

The invention claimed is:

1. A modular joint brace assembly, comprising:
a brace comprising:
a first panel, a second panel, and a third panel, the first panel comprising a first end and a second end opposite to the first end, the first end of the first panel attached to a side of the second panel and the second end of the first panel attached to a side of the third panel, the second panel comprising a first end and a second end opposite the first end, the third panel comprising a first end and a second end opposite the first end; and
a first mating unit coupled to a top surface of the brace, the first mating unit comprising a first portion that extends a length of the first panel from the first end of the first panel to the second end of the first panel, a second portion that extends a length of the second panel from the first end of the second panel to the second end of the second panel, and a third portion that extends a length of the third panel from the first end of the third panel to the second end of the third panel,
wherein the first end and the second end of the second panel are adapted to couple and the first end and the second end of the third panel are adapted to couple such that the second panel wraps around a portion of a user's body adjacent a first end of a joint, the third panel wraps around a portion of the user's body adjacent a second end of the joint, the first end of the joint being opposite the second end of the joint, and the first panel adjacent the joint between the first and second ends of the joint; and
a wedge comprising:
a first top surface, a second top surface, and a peak, wherein the first top surface adjoins the second top surface to form the peak, and wherein the first and second top surfaces are each substantially planar along a length and width of the first and second top surfaces, and wherein the first and second top surfaces are non-monolithic from other applied modular supports; and
a second mating unit coupled to the first top surface and the second top surface, wherein the second mating unit is adapted to couple with the first portion, the second portion, and the third portion of the first mating unit such that the peak of the wedge aligns with a back portion of the joint thereby supporting at least one or more portions of the user's body.

2. The modular joint brace assembly of claim 1, wherein the wedge comprises an inner joint support comprising:
a first lateral surface that is concavely arcuate to conform to a curvature of the portion of the user's body adjacent the first end or the second end of the joint; and
a third mating unit coupled to the first lateral surface, wherein the second mating unit is removably coupled to the second panel or the third panel such that the inner joint support is positioned on the portion of the user's body adjacent the first end or the second end of the joint at a medial side of the joint thereby supporting the at least one or more portions of the user's body.

3. The modular joint brace assembly of claim 2, wherein the wedge comprises an outer joint support comprising:

a second lateral surface that is concavely arcuate to conform to the curvature of the portion of the user's body adjacent the first end or the second end of the joint; and
a fourth mating unit coupled to the second lateral surface, wherein the third mating unit is removably coupled to the second panel or the third panel such that the outer joint support is positioned on the portion of the user's body adjacent the first end or the second end of the joint at a lateral side of the joint thereby supporting the at least one or more portions of the user's body.

4. The modular joint brace assembly of claim 2, wherein the inner joint support further comprises:
a second lateral surface that is concavely arcuate to conform to the curvature of the portion of the user's body adjacent the first end or the second end of another joint; and
a fourth mating unit coupled to the second lateral surface, wherein the fourth mating unit is removably coupled to the second panel or third panel such that the inner joint support is positioned on the portion of the user's body adjacent the first end or the second end of the other joint at a medial side of the other joint thereby supporting the at least one or more portions of the user's body.

5. The modular joint brace assembly of claim 1, wherein the brace further comprises a mating member coupled to the first end of the second panel on a bottom surface of the brace and adapted to couple with the second portion of the first mating unit at a portion of the second end of the second panel.

6. The modular joint brace assembly of claim 1, wherein the brace further comprises a mating member coupled to the first end of the third panel on a bottom surface of the brace and adapted to couple with the third portion of the first mating unit at a portion of the second end of the third panel.

7. The modular joint brace assembly of claim 1, further comprising four mating members, wherein each of the four mating members are coupled to a bottom surface of the first and second ends of the second and third panels.

8. The modular joint brace assembly of claim 1, wherein the second mating unit comprises substantially parallel strips.

9. The modular joint brace assembly of claim 1, wherein the first portion of the first mating unit comprises two or more substantially parallel strips.

10. The modular joint brace assembly of claim 1, wherein the second portion of the first mating unit comprises two or more substantially parallel strips.

11. The modular joint brace assembly of claim 1, wherein the third portion of the first mating unit comprises two or more substantially parallel strips.

12. The modular joint brace assembly of claim 1, wherein the first panel extends along an axis offset from a lateral centerline of at least one of the second panel and the third panel.

13. The modular joint brace assembly of claim 1, wherein a length of the second panel is longer than a length of the third panel.

14. The modular joint brace assembly of claim 1, wherein a first end of the first portion of the first mating unit intersects with a side portion of the second portion of the first mating unit and a second end opposite the first end of the first portion of the first mating unit intersects with a side portion of the third portion of the first mating unit.

15. The modular joint brace assembly of claim 1, wherein the second panel and the third panel are substantially parallel and the first panel is substantially perpendicular to the second and third panels.

16. The modular joint brace assembly of claim 1, wherein the second panel has a length being shorter than the first panel.

17. A modular joint brace assembly, comprising:

a brace comprising:

a top portion and a bottom portion, the top portion adapted to wrap around a portion of a user's body adjacent a first end of a joint, the bottom portion adapted to wrap around a portion of the user's body adjacent a second end of the joint, the first end of the joint being opposite the second end of the joint;

a first mating unit comprising a first portion coupled to a top surface of the top portion and a second portion coupled to a top surface of the bottom portion;

an inner joint support comprising:

a first lateral surface that is concavely arcuate to conform to a curvature of the portion of the user's body adjacent the first end or the second end of another joint; and at least one second mating unit comprised of at least one strip coupled to the first lateral surface and extending circumferentially along a length of the first lateral surface, wherein the at least one second mating unit is removably coupled to the first portion or the second portion of the first mating unit such that the inner joint support is positioned on the portion of the user's body adjacent the first end or the second end of the joint at a medial side of the joint thereby supporting at least one or more portions of the user's body;

wherein the first portion and the second portion of the first mating unit and the second mating unit are each comprised of two parallel strips of hook and loop fasteners.

18. The modular joint brace assembly of claim 17, further comprising an outer joint support comprising:

a second lateral surface that is concavely arcuate to conform to the curvature of the portion of the user's body adjacent the first end or the second end of the joint; and a third mating unit coupled to the second lateral surface, wherein the third mating unit is removably coupled to the first portion or the second portion such that the outer joint support is positioned on the portion of the user's body adjacent the first end or the second end of the joint at a lateral side of the joint thereby supporting the at least one or more portions of the user's body.

19. The modular joint brace assembly of claim 17, wherein the inner joint support further comprises:

a second lateral surface that is concavely arcuate to conform to the curvature of the portion of the user's body adjacent the first end or the second end of another joint; and a third mating unit coupled to the second lateral surface, wherein the third mating unit is removably coupled to the first portion or the second portion such that the inner joint support is positioned on the portion of the user's body adjacent the first end or the second end of the other joint at a medial side of the other joint thereby supporting the at least one or more portions of the user's body.

20. A modular joint brace assembly, comprising:

a brace comprising:

a top portion and a bottom portion, the top portion adapted to wrap around a portion of a user's body adjacent a first end of a joint, the bottom portion adapted to wrap around a portion of the user's body adjacent a second end of the joint, the first end of the joint being opposite the second end of the joint; and a first mating unit comprising a first portion coupled to a top surface of the top portion and a second portion coupled to a top surface of the bottom portion;

an inner joint support comprising:

a first lateral surface that is concavely arcuate to conform to a curvature of the portion of the user's body adjacent the first end or the second end of another joint; and at least one second mating unit comprised of a strip coupled to the first lateral surface and extending circumferentially along a length of the first lateral surface, wherein the at least one second mating unit is removably coupled to the first portion or the second portion of the first mating unit such that the inner joint support is positioned on the portion of the user's body adjacent the first end or the second end of the joint at a medial side of the joint thereby supporting at least one or more portions of the user's body;

an outer joint support comprising:

a second lateral surface that is concavely arcuate to conform to the curvature of the portion of the user's body adjacent the first end or the second end of the joint; and at least one third mating unit comprised of a strip coupled to the second lateral surface, and extending circumferentially along a length of the second lateral surface, wherein the at least one third mating unit is removably coupled to the first portion or the second portion of the first mating unit such that the outer joint support is positioned on the portion of the user's body adjacent the first end or the second end of the joint at a lateral side of the joint thereby supporting the at least one or more portions of the user's body; and a wedge comprising:

a first top surface, a second top surface, and a peak, wherein the first top surface adjoins the second top surface to form the peak; and a fourth mating unit coupled to the first top surface and the second top surface, wherein the fourth mating unit is adapted to couple with the first portion and the second portion of the first mating unit such that the peak of the wedge aligns with a back portion of the joint thereby supporting the at least one or more portions of the user's body;

wherein the first portion and the second portion of the first mating unit, the second mating unit, the third mating unit, and the fourth mating unit are each comprised of two parallel strips of hook and loop fasteners.

* * * * *